United States Patent
Ng

Patent Number: 5,243,966
Date of Patent: Sep. 14, 1993

[54] METHOD FOR SPECULUM SHEATHING AND SHEATHING USE

[76] Inventor: Raymond C. Ng, 1737 Oak Grove, San Marino, Calif. 91108

[21] Appl. No.: 918,710

[22] Filed: Jul. 27, 1992

[51] Int. Cl.⁵ .............................................. A61B 1/32
[52] U.S. Cl. ............................................ 128/3; 128/17; 604/192; 206/363; 206/438; 206/461
[58] Field of Search ............. 128/3, 10, 11, 17, 20, 128/DIG. 24; 604/171, 192, 263; 206/363, 438, 461, 462, 466

[56] References Cited

U.S. PATENT DOCUMENTS

| | | | |
|---|---|---|---|
| 3,128,920 | 4/1964 | Volckening et al. | 604/192 |
| 3,407,928 | 10/1968 | Watts, Jr. | 206/462 X |
| 3,759,370 | 9/1973 | Blatz | 206/466 X |
| 3,851,642 | 12/1974 | McDonald | 128/18 |
| 4,597,382 | 7/1986 | Perez, Jr. | 128/17 |
| 4,878,486 | 11/1989 | Slater | 128/11 |
| 4,972,825 | 11/1990 | Vescovd, Jr. | 128/10 |
| 5,007,409 | 4/1991 | Pope | 128/3 X |

*Primary Examiner*—Richard J. Apley
*Assistant Examiner*—Donna L. Maraglio
*Attorney, Agent, or Firm*—William W. Haefliger

[57] ABSTRACT

A method for sheathing speculum arms, utilizing the combination comprising a holder sheet structure having spaced sections; first and second sheaths extending in substantially parallel relation between the sections, the sheaths respectively associated with the sections, the sheaths defining entrance openings for penetration by the respective arms whereby the arms are insertible into the sheaths, to carry the sheaths; and the holder sheet structure then being separable from the sheaths whereby the speculum arms carrying the sheaths are then usable for vaginal examination.

3 Claims, 2 Drawing Sheets

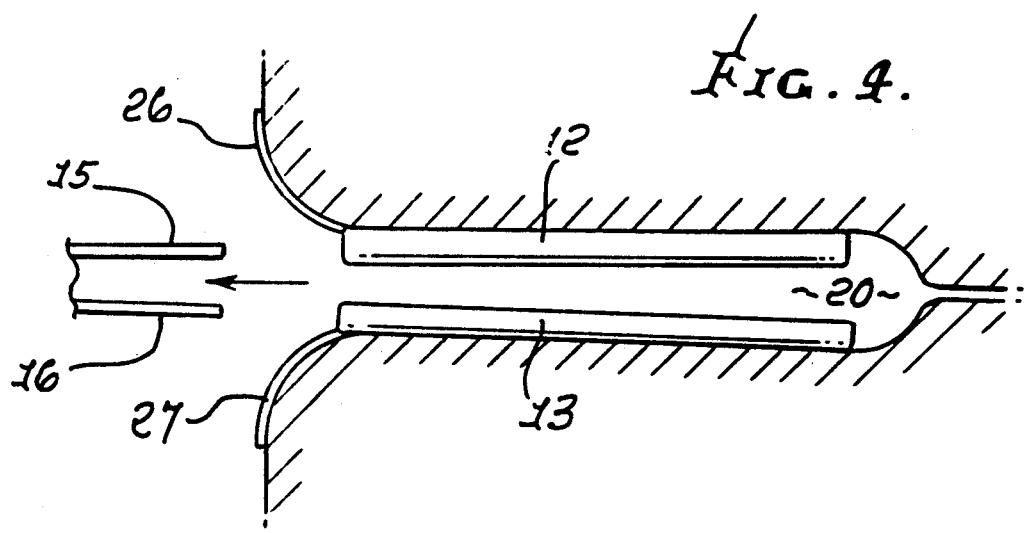
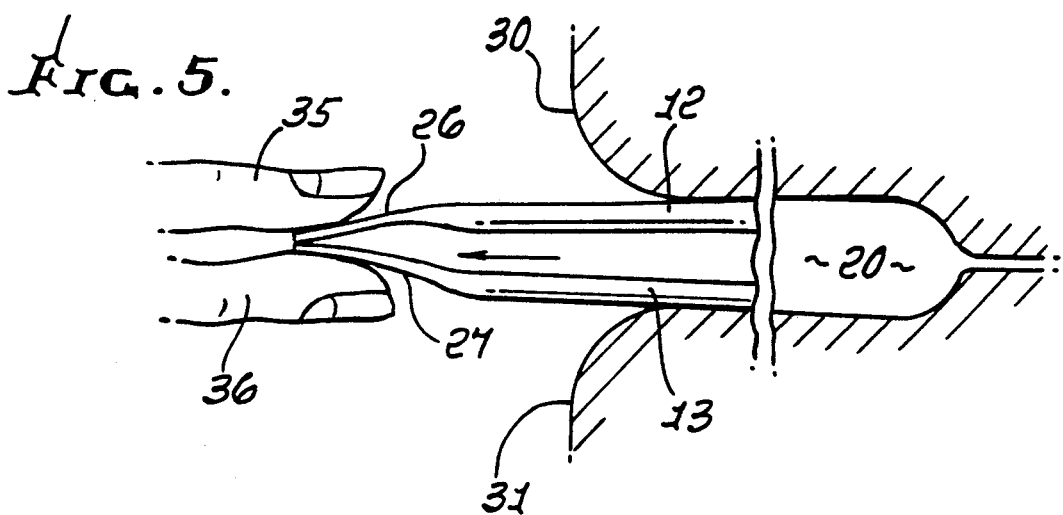
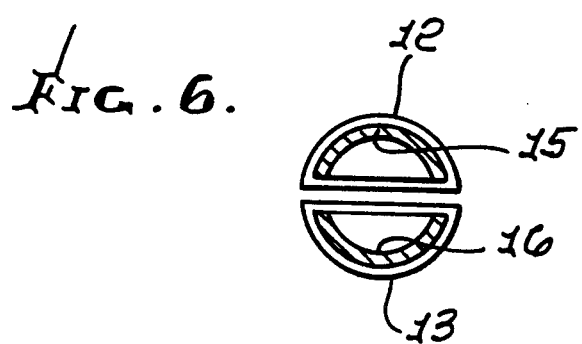

METHOD FOR SPECULUM SHEATHING AND SHEATHING USE

BACKGROUND OF THE INVENTION

This invention relates generally to use of a speculum as during vaginal and/or uterine examination and more specifically to protection of pivoted speculum arms during such examination.

During such examinations, manually manipulated speculum arms or blades are commonly contaminated with blood, mucus and other vaginal debris. Upon removal of the speculum arms, they must be dealt with, i.e. moved to a cleansing zone, cleansed or for example wiped, washed, and sterilized. This procedure is objectionably messy and time consuming, and can become dangerous to staff who must handle the speculum, from the standpoint of AID's contamination of blood or other pathogens on the speculum. There is need for apparatus and procedure or method which obviate these problems and difficulties.

SUMMARY OF THE INVENTION

It is a major object of the invention to provide improved apparatus and method meeting the above needs. Basically, the apparatus of the invention comprises:

a) holder sheet structure having spaced sections, b) first and second sheaths extending in substantially parallel relation between the sections, the sheaths respectively associated with the sections, the sheaths defining entrance openings for penetration by the respective arms whereby the arms are insertible into the sheaths, to carry the sheaths, c) the holder sheet structure then being separable from the sheaths whereby the speculum arms carrying the sheaths are then usable for vaginal examination.

As will be seen, the sheaths are typically initially respectively removably attached to the sections, and may consist of flexible plastic film.

It is another object to provide the holder sheet structure to comprise two interconnected sheets forming the sections which are easily manually positioned to in turn position the sheaths in alignment with the speculum arms for simultaneous insertion into the sheaths. Such holder sheet structure may comprise a single sheet folded to form two sections, the sheet being much stiffer than the flexible sheaths.

Yet another object is to provide a first flap associated with the sheath to project from a first locus proximate the first sheath entrance opening, for protective application to a patient's body during vaginal examination. In addition, a second flap may be provided in association with the second sheath to project from a second locus proximate the second sheath entrance opening, for protective application to a patient's body during vaginal and/or uterine examination.

The method of the invention typically includes the steps:

i) inserting the speculum arms into the sheaths, substantially simultaneously, while using the holder sheet to position the sheaths, ii) separating the holder sheet from said sheaths, while the sheaths remain in protectively sheathed relation with the arms, iii) employing the sheathed speculum arms in vaginal examination, iv) withdrawing the speculum arms endwise from the sheaths while the sheaths remain in the vagina whereby the speculum arm remains relatively clean, v) and withdrawing the sheaths from the vagina, for disposal.

Alternatively, the sheaths may be withdrawn with the speculum arms and may be easily removed from the speculum arms, after use. The method may include deploying a first flap associated with the first sheath into protective application to the patient's body at the vestibule or anterior genitalia, during vaginal examination; and such method may also include deploying a second flap associated with the second sheath into protective application to the patient's body at the perineum, during vaginal examination. Accordingly, the physician conducting the vaginal examination is fully protected from contact with body discharges including possibly contaminated blood.

Yet another object is to provide such sheaths which are dark in color and non-reflecting surfaced to enable laser surgery, obviating need for a molded plastic speculum, the latter being extremely expensive.

These and other objects and advantages of the invention, as well as the details of an illustrative embodiment, will be more fully understood from the following specification and drawings, in which:

DRAWING DESCRIPTION

FIG. 4 is a view like FIG. 3 showing withdrawal of the speculum arms from the sheath, in the cavity;

FIG. 5 is a view like FIG. 4 showing manual withdrawal of the two sheaths, from the cavity; and FIG. 6 is a cross section taken across two speculum arms, each covered by a sheath.

DETAILED DESCRIPTION

Figure 1:
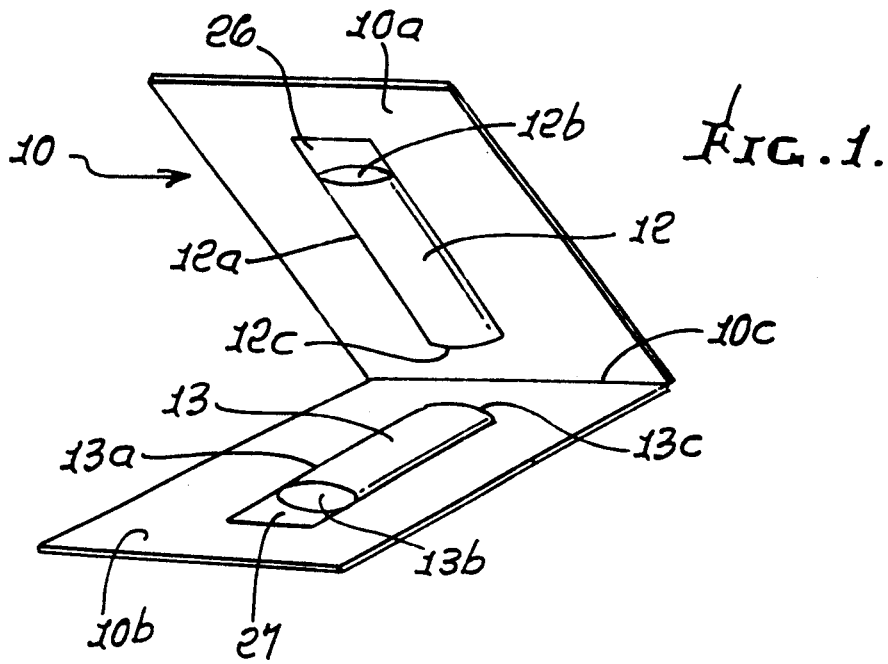
FIG. 1 is a perspective view of a holder sheet with two sections supporting two sheaths.

FIG. 1 shows a holder sheet structure 10 having spaced flat sheet sections 10a and 10b, typically connected by a fold 10c. The holder may consist of cardboard or other relatively stiff material.

Figure 2:
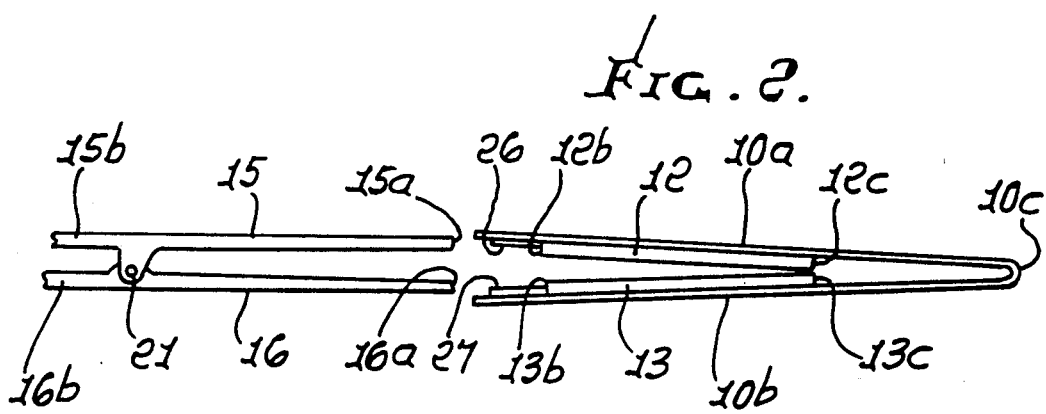
FIG. 2 is an edge view of the FIG. 1 holder sheet showing the sheaths aligned with the speculum arms, respectively.

The sections 10a and 10b carry first and second sheaths 12 and 13, extending in generally flat (collapsed) condition. The sheaths typically consist of film plastic material (one example being surgical glove plastic film), and they may be edge adhered to the sheets, as along edges 12a and 13a which also define longitudinal central zones on 10a and 10b. The sheaths define entrance openings at 12b and 13b, the opposite ends 12c and 13c of the sheaths being closed. Openings 12b and 13b are penetrable by the ends 15a and 16a of speculum arms 15 and 16, FIG. 2 showing the sections 10a and 10b being partly closed together to position the sheaths in generally parallel relation, aligned with the speculum arms to receive endwise sliding penetration of those arms. Once the arms are substantially fully penetrated into the plastic sheaths, the holder sheet structures 10a and 10b can be pulled off or stripped away, the adhering edges 12a and 13a being frangible, leaving the sheaths fully supported on the speculum arms, for vaginal cavity examination.

Figure 3:
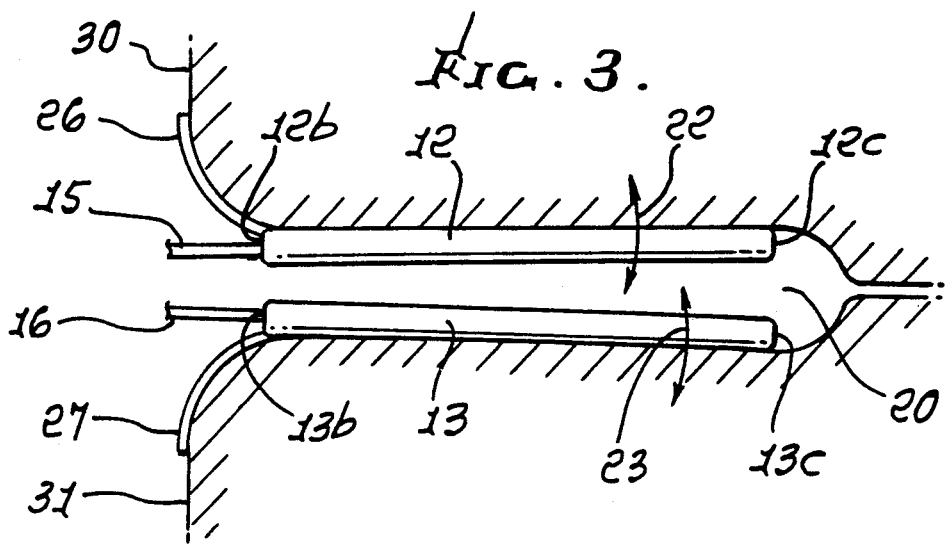
FIG. 3 is a section showing placement of the sheathed speculum arms in a vaginal cavity.

FIG. 3 shows such examination, with the sheathed arms 15 and 16 inserted into cavity 20. See the sheaths 12 and 13 covering those portions of the arms in the cavity. The arms are typically pivoted as at 21 (see FIG. 2) allowing arm relative expansion by manipulation of arm portions 15b and 16b by the gynecologist, during examination. See arm movement direction indicated by arrows 22 and 23, in FIG. 3. FIG. 6 shows the C-shaped cross-section arms 15 and 16, covered by the closely fitting sheaths 12 and 13.

FIG. 3 also shows a first plastic film flap 26 integral with sheath 12, as attached thereto, near entrance 12b; and a second plastic film flap 27 integral with sheath 13, as attached thereto, near entrance 13b. Flap 26 may be protectively folded over or applied to the groin area 30 above the vaginal entrance, as seen in FIG. 3; and flap 27 may be protectively folded over or applied to the groin area 31 below the vaginal entrance. This provides added protection to the physician and nursing staff, during the examination.

FIG. 4 shows slide-out extraction of the smooth surfaced speculum arms 15 and 16 from the sheaths 12 and 13, while they remain in cavity 20. The arms are substantially clean as they have not come into contact with vaginal surfaces, debris, blood, etc., in the cavity. Therefore, they are easily cleaned and sterilized by the nursing staff, without requiring objectionable cleaning of soil substance from the cavity. FIG. 5 shows the two sheaths being pulled from the cavity 20, as by the physician's or nurses fingers 35 and 36, pressing the two flaps together, and pulling, as indicated. The withdrawn soiled sheaths are easily disposed of, without cleaning.

The basic method of use includes the steps:

$x_1$) employing said sheathed speculum arms in vaginal examination, $x_2$) withdrawing the speculum arms endwise from the sheaths while the sheaths remain in the vagina whereby the speculum arms remain relatively clean, $x_3$) and withdrawing the sheaths from the vagina, for disposal.

The sheathing may be transparent, or opaque; and may be darkened for use in laser surgery, if desired.

The invention is also applicable to a speculum which incorporates only one arm—i.e. a single sheath on a single arm. Two flaps as at 26 and 27 may then be attached to a single sheath, near its entrance.

As referred to, the sheaths can be removed from the speculum arms after vaginal examination, for ready and easy disposal.

A single sheath may be employed on a single arm, in a similar way, if desired, for such examination.

I claim:

1. A method of using apparatus for sheathing speculum arms, and employing:
    a) holder sheet structure comprising a first substantially rigid sheet section, a second substantially rigid sheet section attached to and foldable over said first sheet section in order to be aligned with said first sheet section, each of said sections defining a longitudinal central zone, said zones also aligned with each other, one substantially on top of the other, when said first and second sections are in a folded configuration.
    b) first and second sheaths respectively extending in substantially parallel relation with said zones, said sheaths respectively associated with said zones to be removably attached to said sheet sections, the sheaths defining first and second entrance openings for penetration by a pair of vaginal speculum arms whereby the arms are insertible into the sheaths, to carry the sheaths,
    c) the holder sheet structure then being completely separable from the sheaths whereby the speculum arms carrying the sheaths are then usable for vaginal examination, said method including the steps:
        i) inserting the speculum arms into said sheaths, substantially simultaneously, while using said holder sheet to position the sheaths,
        ii) separating said holder sheet from said sheaths, while the sheaths remain in protectively sheathed relation with said arms,
        iii) employing said sheathed speculum arms in vaginal examination,
        iv) withdrawing the speculum arms endwise from the sheaths while the sheaths remain in the vagina whereby the speculum arm remains relatively clean
        v) and withdrawing the sheaths from the vagina, for disposal.

2. The method of claim 1 wherein a first flap is associated with the sheath to project from a first locus proximate the first sheath entrance opening, for protective application to a patient's body during vaginal examination and including the step of deploying said first flap into protective application to the patient's body at the anterior genitalia, during vaginal examination.

3. The method of claim 2 wherein a second flap is associated with the second sheath to project from a second locus proximate the second sheath entrance opening, for protective application to a patient's body during vaginal examination, and including deploying said second flap into protective application to the patient's body at the perineum, during vaginal examination.

* * * * *